(12) United States Patent
Yoshimine et al.

(10) Patent No.: US 7,501,744 B2
(45) Date of Patent: Mar. 10, 2009

(54) CHIP-BASED PIEZOELECTRIC RESONATOR AND LIQUID-PHASE SENSOR

(75) Inventors: Hiroshi Yoshimine, Yokohama (JP); Hiroyuki Sota, Tokyo (JP)

(73) Assignees: GE Healthcare Bio-Sciences K.K., Tokyo (JP); Yoshio Okahata, Kawasaki-shi (JP)

( * ) Notice: Subject to any disclaimer, the term of this patent is extended or adjusted under 35 U.S.C. 154(b) by 0 days.

(21) Appl. No.: 10/532,876

(22) PCT Filed: Oct. 24, 2003

(86) PCT No.: PCT/JP03/13629

§ 371 (c)(1),
(2), (4) Date: Oct. 14, 2005

(87) PCT Pub. No.: WO2004/040268

PCT Pub. Date: May 13, 2004

(65) Prior Publication Data

US 2006/0091763 A1   May 4, 2006

(30) Foreign Application Priority Data

Oct. 31, 2002 (GB) ................................ 0225353.2

(51) Int. Cl.
*H01L 41/053* (2006.01)
(52) U.S. Cl. ..................... 310/340; 310/348
(58) Field of Classification Search ............. 310/340, 310/337, 338
See application file for complete search history.

(56) References Cited

U.S. PATENT DOCUMENTS 5,421,080 A * 6/1995 Bellavance et al. ............ 29/825
6,196,059 B1   3/2001 Koesslinger et al.
6,384,337 B1 * 5/2002 Drum ...................... 174/102 R
6,647,778 B2 * 11/2003 Sparks ..................... 73/204.26
6,651,488 B2 * 11/2003 Larson et al. ............... 73/61.62
6,748,807 B2 * 6/2004 Yoshiuchi et al. ............. 73/493
6,815,872 B2 * 11/2004 Ingram et al. ............... 310/328
2002/0151082 A1   10/2002 Rosentreter et al.

FOREIGN PATENT DOCUMENTS

WO    WO-02/47246 A    6/2002

OTHER PUBLICATIONS

Konash et al., Anal. Chem., Jun. 9, 1980-Jul. 2, 1980, pp. 1929-1931, XP001184167, Retrieved from the Internet: <URL:http:/pubs.acs.org/cgi-bin/archive.cgi/ancham/1980/52/i12/pdf/ac50062a033.pdf>.
Patent Abstracts of Japan, vol. 16, No. 085, p. 1319, Feb. 28, 1992.
Sauerbrey, Zeitschrift Fuer Physik, Springer Verlag, Berlin, Germany, vol. 155, No. 2, 1959, pp. 206-222.

* cited by examiner

*Primary Examiner*—Quyen P Leung
*Assistant Examiner*—Derek J Rosenau
(74) *Attorney, Agent, or Firm*—Birch, Stewart, Kolasch & Birch, LLP

(57) ABSTRACT

The present invention relates to a piezoelectric resonator system comprising a plurality of piezoelectric resonator sensors C', C". Each sensor C', C" comprises an oscillator circuit 29', 29" which is surrounded by its own individual conducting shield 44', 44". Each shield 44', 44" is connectable to one pole of the power supply for its respective sensor C', C". These shields 44', 44" prevent electromagnetic radiation from the sensors C', C" from being transmitted through air.

14 Claims, 3 Drawing Sheets

CHIP-BASED PIEZOELECTRIC RESONATOR AND LIQUID-PHASE SENSOR

TECHNICAL FIELD OF INDUSTRIAL APPLICATION

The present invention relates to chip-based piezoelectric resonator sensors, systems comprising a plurality of piezoelectric resonator sensors and to arrangements and methods for preventing electromagnetic radiation coupling between the piezoelectric resonator sensors in such systems.

PRIOR ART

Piezoelectric acoustic wave devices such as quartz resonators can be utilized as mass sensors on the basis of the principle that a material adsorbed on the electrode surface changes the fundamental oscillation frequency of the oscillator in proportion to the mass of the adsorbate; the change has been proven experimentally to conform to the theoretical formula proposed by Sauerbrey (Sauerbrey, G., Z. phys. 155 (1959), p. 206-222). Owing to the high detection sensitivity predicted by the formula, a micro-measurement method using such a sensor is far superior to general mass measurement methods using mechanical balances, and thus the method has been put into practical use, for example, in quantitative measurement of odorous molecules or aerosols in the gaseous phase.

A piezoelectric resonator is generally a circular or rectangular crystalline plate shaped by cutting along a particular crystal face for a natural characteristic oscillation of the crystal, for example a quartz crystal, and is provided with electrodes made of thin layers of vapour-deposited metal. Depending upon its cutting angle, each crystal plate is designated as an AT, BT, CT, X, or Y cut. The quartz plate is situated between a pair of thin-layer metal electrodes placed symmetrically in parallel. An induction electrical field between the electrodes results in distortion in the quartz crystal, whereas a distortion produces an electrical charge; the so-called piezoelectric phenomenon produces a reversible and steady oscillation.

Usually, the surface area of the quartz plate is wider than that of the electrode. The non-electrode area without the piezoelectric effect on the quartz plate helps to propagate the elastic wave originating at the electrode area while moderately attenuating the wave. Thus, it is an area that is responsible for the so-called "confinement effect." Thus, in designing piezoelectric resonators, the selection of shape and size of the piezoelectric plate is most important in order to reduce unfavourable sub-oscillations such as spurious oscillations caused by adverse effects such as end-face reflection of the plate, etc.

A means of mechanical fixation is necessary for mounting such a piezoelectric resonator for use as a sensor. A piezoelectric resonator element for use as an electronic component used in the gaseous phase is usually designed to be supported by a minute contact area of the piezoelectric plate end face by using a supporting metal lead in order to lower the stress as far as possible in both the directions of the radius and the thickness of the piezoelectric plate. In other words, the elastic wave is attenuated in the vicinity of the end face and the influence of the mounting forces is small; the contact area is taken into consideration to reduce the area as much as possible so as not to impose the mounting forces on the piezoelectric plate.

The first liquid-phase elastic wave element sensor was reported by Basstiaans and his colleague in 1980 (Konash, P. L. and Bastiaans, G. J., Anal. Chem. 52 (1980), p. 1929-1931). Ever since the first report, many studies have been reported on elastic wave element sensors operating in the liquid phase; the technology is applicable to detect substances, as targets under test, including pharmaceutical agents usually dissolved in the liquid phase, and chemical substances such as agricultural pesticides and food additives, as well as bio-functional molecules represented by nucleic acids such as DNA and RNA, and proteins such as antibodies, hormone receptors, and lectins, which function only in the liquid phase, as well as bacteria and other cells.

However, a problem occurs when the piezoelectric resonator, which is an electrical element originally-designed on the assumption of using it in a gaseous phase, is used as a sensor in a conducting solution—namely an electrical short-circuit occurs between the electrodes in solution. In all the previous studies, without exception, it has been necessary to take measures to prevent this short-circuit. Specifically, in a liquid-phase piezoelectric resonator sensor, the one of the pair of electrodes which acts as a detection surface is exposed to the liquid phase, while the other electrode is protected in some way against coming into contact with the solution. Of course as the piezoelectric resonator is an element which is based on the principle of a constant stable elastic oscillation, any mechanical constructions to prevent the electrode from coming into contact with the solution, which interfere with the oscillation of the piezoelectric resonator, should be definitely avoided.

The high-quality frequency stability of a piezoelectric resonator as an elastic wave element is represented by a high Q (quality factor). The Q markedly decreases as the degree of interference with the oscillation of the piezoelectric resonator increases. In addition, in the liquid-phase sensor, in which the piezoelectric plate is exposed to a liquid with a high viscosity as compared with gas, being in contact with liquid itself may have an interfering effect and, as a consequence, the Q may decrease greatly; the Q may also decrease to the minimum due to an improper mechanical construction. In other words, in the worst case the oscillation might stop.

Chip based piezoelectric resonators have been developed (see WO02/47246) in which the piezoelectric resonator is positioned flat on a substrate and is bonded to the substrate by an elastic bonding agent applied around its periphery. This elastic bonding allows oscillation in the plane of the crystal. The substrate can form the floor of a flow cell, with the face of the piezoelectric resonator that faces away from the substrate exposed to the fluid in the flow cell. Electrical connections can be provided on the face of the piezoelectric resonator that faces towards the substrate and leads can pass through one or more through holes in the substrate for connection to an oscillator circuit. Sensor systems can be made in which two or more chip-based piezoelectric crystal resonator flow cells are arranged in parallel or in series.

When two or more piezoelectric resonator sensors are used in a system then there is a risk of coupling occurring. In other word, there is a risk that the output signal from a sensor may be influenced by the signal from another sensor. There are 4 primary ways in which this might occur. These are:
a) acoustic wave transmission though a waveguide, e.g. the liquid filled tube connecting the sensors:
b) acoustic wave transmission through the air:
c) electromagnetic wave transmission through a wave guide and
d) electromagnetic wave transmission through the air.

The dominant coupling mode was found by experiments. In a first experiment two chip-based piezoelectric resonator sensors were placed 5 mm apart in a metal chamber with buffer liquid flowing between them (see FIG. 2). They were excited and their signals recorded. When the excitation of the first sensor was changed, a change in the second sensor's output signal was recorded (see FIG. 3), showing that there was coupling between the two sensors.

In a second experiment, the two sensors were placed 1 m apart in separate metal chambers. In this case a change in the excitation of the first sensor did not cause a change in the signal of the second sensor, showing that in this instance there was no coupling between the sensors and that coupling was a function of electromagnetic shielding.

Problem to be Solved by the Invention

Signal coupling between the piezoelectric resonator sensors in systems comprising a plurality of piezoelectric resonator sensors is a problem. In particular, electromagnetic wave transmission through the air has proven to be the dominant cause of signal coupling for such systems. The purpose of the present invention is to provide a piezoelectric resonator sensor system that overcomes the problem of signal coupling caused by electromagnetic wave transmission through the air without requiring the piezoelectric resonators to be spaced a large distance (e.g. 1metre) apart.

DISCLOSURE OF THE INVENTION

In the present application of the invention, a new design is presented which attempts to overcome these problems that were unsolved by the prior art.

An object of the present invention is to provide a piezoelectric resonator system comprising a plurality of piezoelectric resonator sensors in which coupling between the piezoelectric resonator sensors by electromagnetic wave transmission through the air is reduced or prevented. This is achieved by a method according to claim 1, and a device according to claim 4 in which shielding is used to prevent electromagnetic wave transmission through the air.

The present invention will be illustrated below by means of examples of embodiments of the invention and drawings.

DESCRIPTION OF THE PRESENT INVENTION

Figure 1:
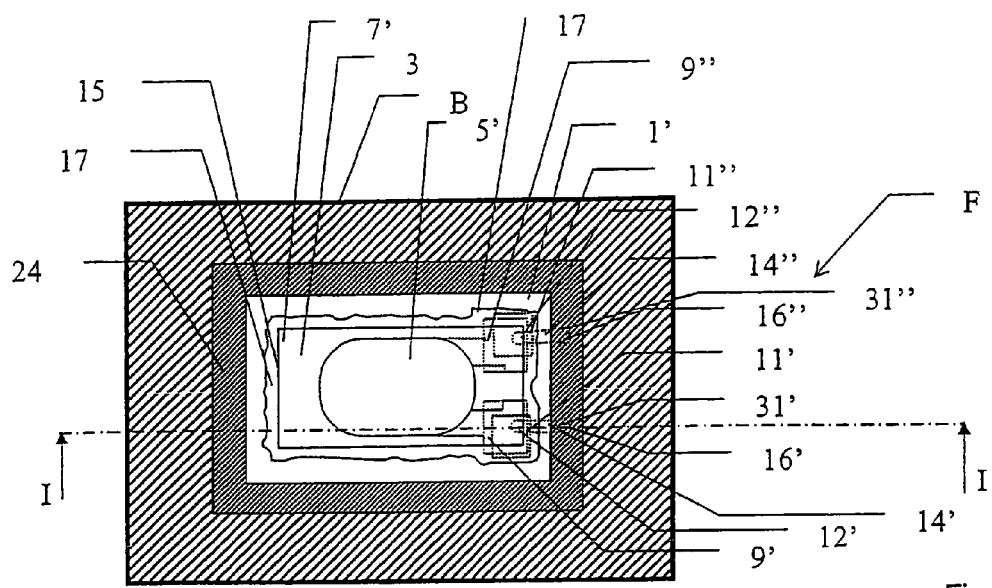
FIG. 1a) is a sectional view along the line II-II in FIG. 1b) of a prior art flow-type chip-based piezoelectric resonator sensor.
FIG. 1b) is a sectional view along line I-I in FIG. 1a)
Figure 1:
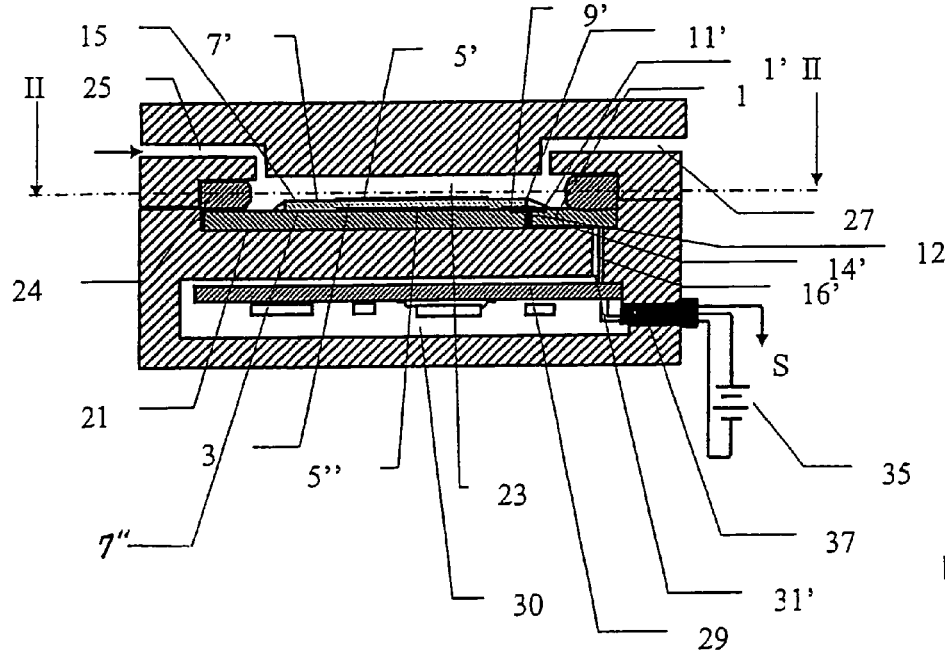

FIG. 1a) is a sectional plan view along line II-II in FIG. 1b) showing a first embodiment of a prior art chip piezoelectric resonator flowcell sensor F, and FIG. 1b) is a sectional view along the line I-I indicated in FIG. 1a). In these figures, a rectangular piezoelectric resonator 3 is placed on the upper surface 1' of a substrate 1. Substrate 1 is made of any material which is rigid, non-conducting or able to retain a non-conducting coating, non-soluble in the liquids being tested and preferably inexpensive and easy to work with. Many engineering plastics, metals and ceramics are suitable for this use, in particular the types used for making circuit boards. The piezoelectric resonator 3 has a detection electrode 5' on a first surface 7' and a non-detection electrode 5" on the opposite second surface 7" i.e. in this case the side facing towards the upper surface 1' of the substrate 1. As an example, the piezoelectric resonator 3 may be in the order of 4 mm long, 1.6 mm wide and 60μm thick, other dimensions and shapes are of course possible. Thus the first and second surfaces have an area of 6.4 mm$^2$ and the side-wall 15 of the resonator is 60μm deep.

In order to make an electrical connection to the corresponding portion of the substrate 1, electrodes 9', 9" made of a thin metal layer, are connected respectively to the detection electrode 5', non-detection electrode 5". The electrode 9' extends across the surface of the piezoelectric resonator to its edge, over the edge and down the side of the piezoelectric resonator 3 and around the bottom edge of the side-wall to the underside of the piezoelectric resonator where each of electrodes 9', 9" is connectable, preferably by using a small amount of electrically conducting bonding agent (not shown), to one of a pair of first terminals 11', 11" on the upper surface of the substrate. These first terminals 11', 11" are preferably formed of a thin layer of metal on the upper surface of the substrate. Each of these first terminals is connectable by means of an electrical connection such as vias 12', 12" through the substrate to one of a pair of second terminals 14', 14" placed on the opposite surface of the substrate. Each of these second terminals is in contact with one of a pair of contact pins 16', 16" which are in electrical contact with the oscillator circuit 29 described below.

In order to prevent a short circuit between the detection electrode 5' and the non-detection electrode 5" caused by an electrically conducting fluid coming in contact with the non-detection electrode placed on the back of the piezoelectric resonator 3, the side-wall 15 of the piezoelectric resonator 3 is flexibly fixed and sealed along the whole of its circumference to the substrate 1 by using an elastic bonding agent 17. This bonding agent is preferably not soluble in the liquids being tested and can be, for example, a silicon-resin bonding agent. The cured bonding agent is elastic enough to allow the resonator's stabilised motion while at the same time being stiff enough to prevent the resonator from wandering.

Substrate 1 is mounted on the floor 21 of a cavity 23 in flowcell sensor body B with piezoelectric resonator 3 exposed to the contents of the cavity 23. A gasket 24 seals the cavity and also holds the substrate 1 in place. Cavity 23 is provided with an inlet channel 25 and an outlet channel 27. Inlet channel 25 can be connected to a source of fluid (not shown) and outlet channel 27 can be connected to a fluid-receiving vessel 28 (not shown). Flowcell sensor F is provided with oscillator circuit 29 for driving the piezoelectric resonator 3. Resonator 3 is connected to terminals 11', 11' by contact with contact pins or leads 16', 16" which pass through vias 31', 31" in floor 21 to oscillator circuit 29 inside oscillator circuit chamber 30. Oscillator circuit 29 is connectable to a power supply, e.g. battery 35 and the output signal S of the piezoelectric resonator 3 is outputted from the flowcell sensor F by means of a connector 37. Signal S may be transmitted to a control device (not shown) by a photo-coupler (not shown) in order to prevent electrical interference.

Figure 2:
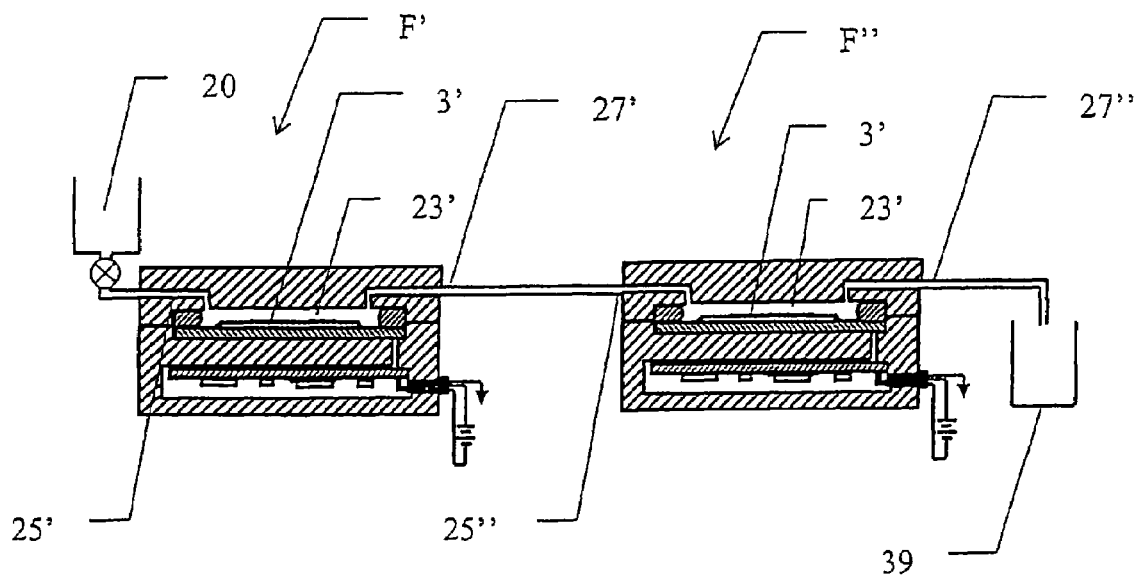
FIG. 2 is a schematic illustration showing two prior art chip-based piezoelectric resonator sensor flowcells connected in series.

FIG. 2 is a sectional view showing an example of a flow-type liquid-phase piezoelectric resonator sensor system using a plurality, in this case a first and a second chip-based piezoelectric resonator flowcell sensor F', F'" are connected in series. The outlet channel 27' of the first flowcell sensor F' is connected to the inlet channel 25" of the second flowcell sensor F".

The outlet channel 27" of the flowcell sensor F" leads to waste or a collection vessel 39. During use, liquid to be analysed is supplied by a reservoir 20 (or other input device such as a syringe or pump) to the inlet channel 25' of the first flowcell F'. It then flows through the cavities 23', 23", thereby coming into contact with the piezoelectric resonators 3'-3", and subsequently leaves the system to waste or a collection vessel 39 via the outlet channel 27" of flowcell sensor F".

Figure 3:
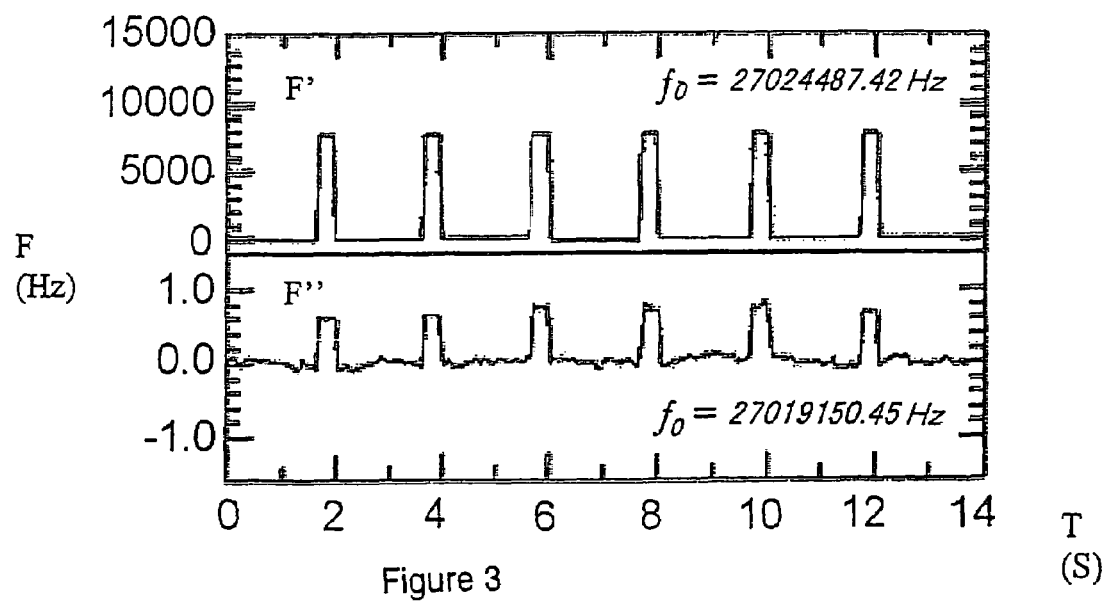
FIG. 3 shows coupling between the flowcells of FIG. 2.

FIG. 3 shows that flowcell sensor F" exhibited pulse-shaped frequency changes when the pulse-shaped frequency changes were imposed on flowcell sensor F'. This occurred even when the flow path was not filled with an electrolyte which leads to the conclusion that the coupling was the product of electromagnetic radiation transmitted through the air between the flowcell sensors.

Figure 4:
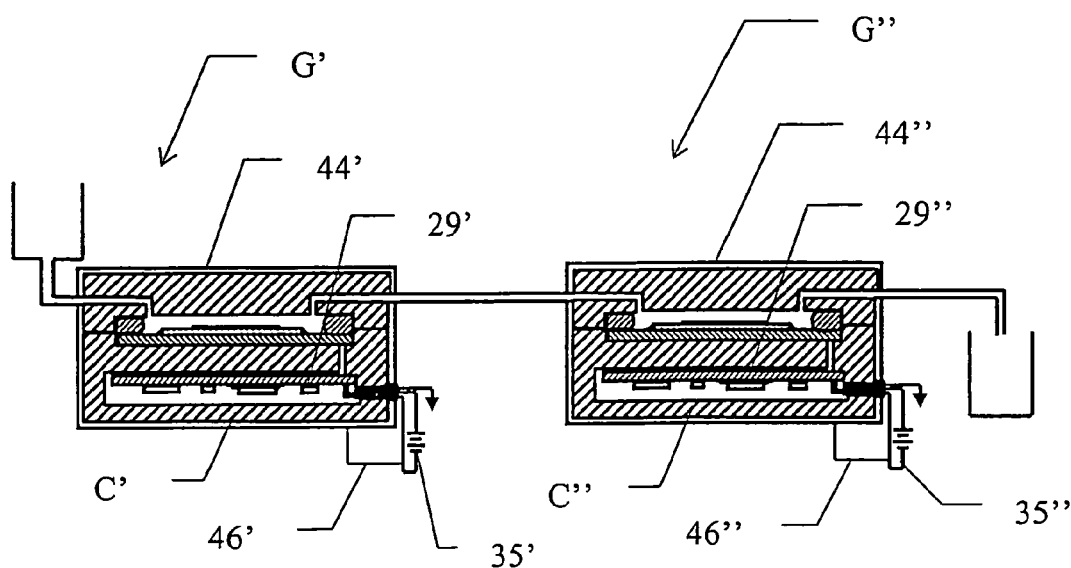
FIG. 4 is a schematic illustration showing two chip-based piezoelectric resonator sensor flowcells according to a first embodiment of the present invention connected in series; and, FIG. 5 shows the absence of coupling between the flowcells of FIG. 4.

FIG. 4 shows a flow-through sensor system in accordance with a first embodiment of the present invention. Elements of this system which are similar to elements of the system of FIG. 2 have been given the same reference numerals. In order to reduce electromagnetic wave transmission though the air between the sensors G', G" each sensor G', G" is individually shielded by means of its own conducting shield 44', 44". Shields 44', 44" can be made of metal tape and substantially completely surrounds each of their respective sensors G', G". Shield 44' is connected to the negative pole of the battery 35' of sensor G' by a conductor 46', and shield 44" is connected to the negative pole of the battery 35" of sensor G" by a conductor 46". Each shield 44', 44" prevents electromagnetic radiation from leaving or entering the respective sensor G', G" and thereby prevents electromagnetic wave transmission between the sensors through the air.

Figure 5:
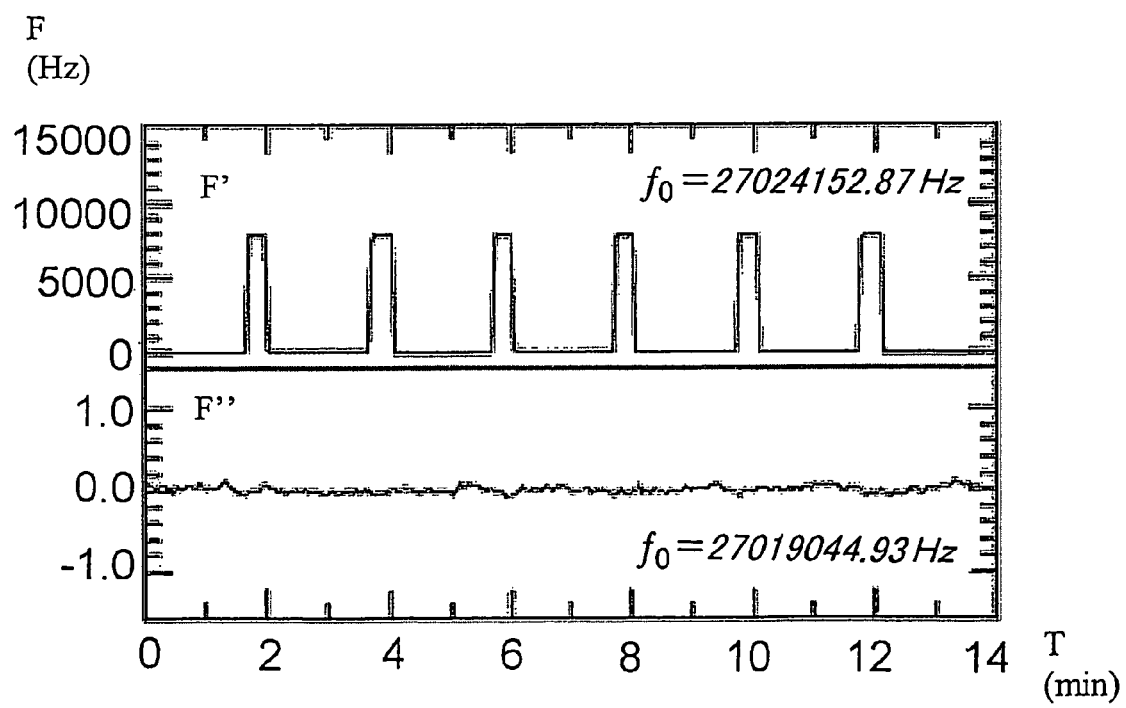

FIG. 5 shows that flowcell sensor G" did not exhibit pulse-shaped frequency changes when the pulse-shaped frequency changes were imposed on flowcell sensor G'. This shows that the coupling that was the product of electromagnetic radiation transmitted through the air between the flowcell sensors is prevented by shielding measures in accordance with the present invention.

Shields 44', 44" can be made of any suitable conducting material. In one embodiment of the present invention, each sensor housing is made of an insulating material such as plastic coated with a conducting material such as a metal. The plastic/metal composite housing is arranged such that the surface exposed to the liquid in the sensor are made of plastic and are non-conducting, while the outer surface of the housing is metal. In this arrangement, the plastic material prevents an electrical short circuit between the sensor surface and the oscillation circuit through the liquid in the sensor.

In a further embodiment of the present invention, the shielding is provided by spraying the outer surface of each sensor housing with a conducting material, such as metal In yet another embodiment of the present invention, only the oscillator circuit cavity of the flowcell is shielded, preferably by applying shielding material to the interior walls of said cavity.

In a further embodiment of the present invention, both the oscillator circuit cavity and the complete flowcell are shielded.

The above mentioned embodiments are intended to illustrate the present invention and are not intended to limit the scope of protection claimed by the following claims.

The invention claimed is:

1. Method for preventing signal coupling between two or more flow-through type chip-based mounted piezoelectric resonator sensors used in an electrically conductive liquid, wherein each of the sensors has a flowcell body provided with its own resonator connected to its own single oscillator circuit and its own single power supply, said resonator being on a single substrate, comprising:
   providing each sensor with its own, individual conducting shield which substantially surrounds said flowcell body,; and
   making an inner wall of a flow tube and each cavity out of a non-conducting material;
   wherein said conducting shields of different sensors are not interconnected, and each flow tube interconnecting adjacent sensors is not shielded.

2. Method in accordance with claim 1, wherein said conducting shield is made of metal tape.

3. Method in accordance with claim 1, wherein an individual sensor housing for each sensor is made of plastic, and the plastic is coated with said individual conducting shield.

4. Method in accordance with claim 1, wherein said individual conducting shield is made by spraying, with a conducting material, an outer surface of an individual housing for said each sensor.

5. Method in accordance with claim 1, wherein an oscillator circuit cavity for said each sensor is shielded by applying shielding material to interior walls of said cavity.

6. Method in accordance with claim 1, wherein said conducting shield is connected to one pole of the power supply.

7. Method in accordance with claim 6, wherein said flowcell body is made of a non-conducting material.

8. Method in accordance with claim 6, wherein the poles connected to said individual conducting shields of said sensors have the same polarity in said single power supplies.

9. Method in accordance with claim 1, wherein individual conducting shielding material is applied to an interior wall of an oscillator circuit cavity for each sensor.

10. Piezoelectric resonator sensor comprising:
    a flowcell body comprising a resonator connected to a single oscillator circuit, wherein said flowcell body is made of a non-conducting material; and
    a single power supply, wherein said body is substantially surrounded by a conducting shield connected to one pole of the power supply,
    wherein an inner wall of a cavity, an inlet channel and an outlet channel are insulated from said shield,
    wherein said conducting shield of said piezoelectric resonator sensor is not interconnected with conducting shields of different sensors, and
    flow tubes interconnect said piezoelectric resonator sensor to adjacent sensors, and each of said flow tubes is not shielded.

11. Sensor in accordance with claim 10, wherein said conducting shield is made of metal tape.

12. Sensor in accordance with claim 10, wherein a sensor housing for said piezoelectric resonator sensor is made of plastic, and the plastic is coated with said conducting shield.

13. Sensor in accordance with claim 10, wherein said conducting shield is made by spraying, with a conducting material, an outer surface of a housing for said piezoelectric resonator sensor.

14. Sensor in accordance with claim 10, wherein an oscillator circuit cavity for said piezoelectric resonator sensor is shielded by applying shielding material to interior walls of said cavity.

* * * * *